US007625940B2

(12) United States Patent
Solomon

(10) Patent No.: US 7,625,940 B2
(45) Date of Patent: Dec. 1, 2009

(54) METHOD OF TREATING HYPERTENSION WITH A VERY LOW DOSE OF CHLORTHALIDONE

(75) Inventor: Lawrence Solomon, Boca Raton, FL (US)

(73) Assignee: Accu-Break Technologies, Inc., Plantation, FL (US)

( * ) Notice: Subject to any disclaimer, the term of this patent is extended or adjusted under 35 U.S.C. 154(b) by 906 days.

(21) Appl. No.: 11/173,544

(22) Filed: Jul. 1, 2005

(65) Prior Publication Data

US 2007/0004792 A1    Jan. 4, 2007

(51) Int. Cl.
*A61K 31/405* (2006.01)
(52) U.S. Cl. .................................................. 514/415
(58) Field of Classification Search .................. 514/416
See application file for complete search history.

(56) References Cited

U.S. PATENT DOCUMENTS 3,055,904 A    9/1962    Graf et al.
5,948,799 A    9/1999    Cropp

OTHER PUBLICATIONS

Carter, B. L., Ernst, M. E., Cohen, J. D., "Hydrochlorothiazide versus chlorthalidone: evidence supporting their interchangeability." Hypertension (2004) 43:4-9. USA.
Materson, BJ, et al., Dose Response to Chlorthalidone in Patients With Mild Hypertension. Clinical Pharmacology and Therapeutics (1978) vol. 24(2):192-198.

*Primary Examiner*—Raymond J Henley, III
(74) *Attorney, Agent, or Firm*—Ted Whitlock

(57) ABSTRACT

A method for the treatment of systemic arterial hypertension, which is based on the oral administration to a patient suffering from systemic arterial hypertension either in an amount of chlorthalidone of 2.5-10 mg daily, alone or in novel combination use with another anti-hypertensive.agent.

11 Claims, No Drawings

METHOD OF TREATING HYPERTENSION WITH A VERY LOW DOSE OF CHLORTHALIDONE

INTRODUCTION

Methods of administration of lower doses of chlorthalidone are described as treatment for systemic arterial hypertension than have previously been divulged, either as monotherapy or in concurrent use including novel fixed-dose combinations with another antihypertensive agent.

BACKGROUND OF THE INVENTION

The long-acting diuretic chlorthalidone has been known for decades as an effective treatment to lower elevated arterial blood pressure (arterial hypertension or hypertension). The compound received U.S. Pat. No. 3,055,904, which disclosed a dosage range of 50 mg to 200 mg orally one to three times a day or 100 mg every second day. U.S. Pat. No. 5,948,799 discloses a typical range of chlorthalidone of 6.25-200 mg daily and a preferred range of 12.5 to 100 mg daily for use in the treatment of non-ischemic congestive heart failure in combination with amlodipine and/or digoxin; this patent does not address the treatment of hypertension. In addition, the study supporting said patent involved patients receiving amlodipine, almost all of whom were concomitantly receiving digoxin, and both amlodipine and digoxin are known to have diuretic activity.

Chlorthalidone has been chemically described as: benzenesulfonamide, 2-chloro-5-(2,3-dihydro-1-hydroxy-3-oxo-1H-isoindol-1yl) or 2-chloro-5-(1-hydroxy-3-oxo-1,2-dihydroisoindol-1-yl)-benzenesulfonamide.

The U.S. Food and Drug Administration's (FDA) approved starting dose for hypertension for chlorthalidone is 25 mg daily; this dose is available in the U.S. as an unscored tablet. In the European Union, chlorthalidone is available as a 50 mg scored tablet.

Hypertension is widely acknowledged to be one of the most widespread of all illnesses. There are about 60 million cases of hypertension in the U.S. It is believed that approximately ⅓ of all patients with hypertension in the U.S. are adequately treated, ⅓ are treated but not adequately, and ⅓ are not treated.

The invention is timely because the anomalous position of chlorthalidone in hypertension treatment has led to a need for non-obvious doses of this product to be brought to market. On the one hand, chlorthalidone is widely acknowledged to be the diuretic best documented to provide clinically significant benefits in terms of health outcomes. On the other hand, relatively few prescriptions for chlorthalidone are written in the U.S. It is believed that the lack of appropriate low doses helps explain the lack of medical interest in this drug. The following discussion summarizes how this situation has developed and why there is a medical need for the invention.

Chlorthalidone was extensively studied versus another diuretic, hydrochlorothiazide (HCTZ), in the 1970's, in the Multiple Risk Factor Intervention Trial, a National Institute of Health (NIH)-sponsored study. The investigators concluded that chlorthalidone appeared potentially superior to HCTZ. Subsequently, NIH sponsored four (4) large-scale health outcomes utilizing a diuretic. The diuretic chosen each time was chlorthalidone. The four studies were the Treatment of Mild Hypertension Study (TOMHS), Hypertension Detection and Follow-Up Program (HDFP), Systolic Hypertension in the Elderly Program (SHEP), and the Antihypertensive and Lipid-Lowering Treatment to Prevent Heart Attack Trial (AL-LHAT) study. Of the above studies, the last two utilized starting doses of 12.5 mg of chlorthalidone. However, the patient populations in these two studies were not typical hypertension patients. In SHEP, all patients were at least sixty years old and had systolic hypertension. In ALLHAT, patients had more risk factors than other patients, and there was no placebo group, so that efficacy of the 12.5 mg dose vs. placebo was not tested. In addition, in ALLHAT, all patients were at least 55 years old and the average was 67; thus its results were geared toward the elderly. Dose escalation was the general strategy for SHEP and ALLHAT as needed. Smaller studies of the 12.5 mg dose have been performed, all with trends toward efficacy of that dose in treating hypertension.

At the same time as the above studies were being conducted, HCTZ became the prevalent treatment for hypertension when a diuretic was utilized in the U.S. A commonly provided reason for this is that chlorthalidone was not produced in a dose low enough to avoid metabolic side effects such as hypokalemia and diabetes, whereas HCTZ was developed in a dose as low as 12.5 mg in 1997. It is thus an intention of the inventor to bring to market novel doses of chlorthalidone to treat hypertension that have not been disclosed, and that are freer of side effects than existing chlorthalidone doses, while still providing anti-hypertensive benefits.

Doses of chlorthalidone below 12.5 mg daily have not been studied for the treatment of hypertension. Carter et al., has suggested, without compelling evidence, that 6.25 mg daily may be an appropriate starting dose for elderly patients with hypertension. Carter, B. L., Ernst, M. E., Cohen, J. D., "Hydrochlorothiazide versus chorthalidone: evidence supporting their interchangeability." *Hypertension* 43 (2004): 4-9 (hereafter "Carter").

The failure of Carter to propose a 6.25 mg chlorthalidone dose for hypertension other than for the elderly suggests that efficacy at this dose other than in the elderly (excluding the frail, renally-impaired, or pediatric populations, etc.) would be unexpected. A close reading of the article does not clearly support even the recommendation for the ultra-low dose of 6.25 in the elderly, as the author admits that "the more recent recommendations (are) that the 2 drugs are equipotent," and the author offers 12.5 mg as the starting dose of HCTZ for the elderly. It is well recognized that 6.25 mg of HCTZ is not a predictably effective dose for hypertension.

Evidence of the importance of a novel ultra-low dose of chlorthalidone to treat hypertension may be seen in the study of Materson et al., which found that the incidence of hypokalemia at 12.5 mg of chlorthalidone daily was 45% at 12.5 mg, 35% at 25 mg, 41% at 50 mg, and 42% with 75 mg, all doses once daily. Materson, B. J., Oster, J. R., Michael, U. F., Bolton, S. M., Burton, Z. C., Stambaugh, J. E., Morledge, J. M., "Dose Response to Chlorthalidone In Patients With Mild Hypertension." *Clinical Pharmacology and Therapeutics* Vol. 24, No. 2 (1978): 192-198. The failure of this study to demonstrate a dose relationship of chlorthalidone with regard to hypokalemia suggests the need for lower doses that retain adequate anti-hypertensive effect.

All doses referred to herein are oral doses.

Chlorthalidone, as with other anti-hypertensive agents, is taught to be started at the lowest dose appropriate and then for the dose to be increased as needed. In the case of the Carter article, 6.25 mg is disclosed as a starting dose for the elderly.

The dosages of chlorthalidone referred to herein assume that the formulation does not contain a solubility enhancer. Poly(vinyl pyrrolidone), otherwise known as PVP, has been used in the marketed product Thalitone® to provide greater bioavailability than the standard Hygroton® brand provided.

All formulations described herein relate to standard formulations that have immediate release characteristics and do not utilize PVP or other solubility or absorption modifiers.

SUMMARY OF THE INVENTION

The invention provides a method for the treatment of systemic arterial hypertension ("hypertension"), which comprises orally administering chlorthalidone to an adult patient less than sixty-five (65) years old suffering from arterial hypertension in a daily amount of 2.5-10 mg. The types of hypertension known, for example, as pulmonary arterial hypertension and portal vein hypertension are not objects of the invention. The invention also includes doses of from 2-5 and more preferably from 3-3.25 mg daily for the elderly, such as patients older than 65 years. The type of hypertension being treated may be essential hypertension (i.e., not of specific causation) or secondary (e.g, such as due to renal artery stenosis).

Chlorthalidone per the invention may be administered using any conventional enteral dosage formulation, preferably either in tablet form where conventional excipients such as lactose, microcrystalline cellulose and the like may be used to formulate tablets using conventional techniques (such as those disclosed in Remington's Pharmaceutical Sciences, 20th Ed. which is incorporated by reference) or, in capsule form. Other enteral routes of administration such as per rectum are less preferred. Advantages of the very low doses disclosed herein include without limitation the avoidance of metabolic disturbances; the unmasking of pseudo-hypertension; minimization of hypotensive reactions when chlorthalidone is given as monotherapy; and the ability to add to existing therapy for hypertension in which any diuretic added at even a low dose may lead to excessive hypotension.

Chlorthalidone per the invention may be administered as monotherapy or in conjunction with an additional anti-hypertensive drug such as, without limitation, an angiotensin converting enzyme (ACE) inhibitor (e.g., enalapril, lisinopril, benazepril, ramipril) an angiotensin receptor blocker (ARB) (e.g., losartan, valsartan, candesartan, eprosartan), or an alpha blocker (e.g., prazosin, doxazosin, terazosin); angiotensin converting enzyme inhibitors, e.g. lisinopril, enalapril, ramipril, perindopril, benazepril, captopril; calcium antagonist (calcium channel blocker) e.g. nifedipine, nicardipine, nisoldipine, calcium antagonist: amlodipine (racemic), S-amlodipine, lacidipine, lercanidipine, manidipine, azelnidipine; aldosterone antagonist e.g.: spironolactone, canrenone, eplerenone; beta blocker e.g. carvedilol, nebivolol, atenolol, metoprolol, betaxolol, bisoprolol at appropriate doses such as the doses that are disclosed in the Physicians' Desk Reference (2005) which is incorporated by reference

DETAILED DESCRIPTION OF THE INVENTION

The invention may be manufactured on a suitable tablet press and may for example be produced as a scored tablet, an unscored tablet, or as a capsule. Tablets may be standard homogeneous tablets or may be non-homogeneous layered tablets. Suitable excipients are used in all cases, unless chlorthalidone drug ("neat" drug) without excipients can be used in the tabletting or encapsulating process.

In an example of the invention, a 78 year old man has an elevated arterial blood pressure. The patient receives 3 mg of chlorthalidone daily. In one month, the blood pressure drops moderately but not to goal, but the serum potassium level drops as well to near the lower limit of the desired range. Lisinopril 5 mg daily is added, the blood pressure normalizes, and the serum potassium level rises somewhat. Treatment is continued.

In another embodiment of the invention, a 48 year old patient with an elevated blood pressure begins treatment with chlorthalidone 6.25 mg daily, on which treatment the blood potassium level is satisfactory. The blood pressure drops and treatment is continued.

In another example of the invention, a 75 year old patient is given enalapril 20 mg once daily because of elevated blood pressure. He then receives 3 mg once daily of chlorthalidone. One month later, the blood pressure is lowered and the medications are continued. Three months later, the patient revisits the physician and the blood pressure is again elevated. A third medication, amlodipine, is added and the blood pressure normalizes. All medications are continued. The patient has the benefit of a safe dose of chlorthalidone.

The invention claimed is:

1. A method for the treatment of hypertension, which comprises orally administering chlorthalidone to an adult patient less than sixty-five years old suffering from arterial hypertension in a daily amount of 2.5-10 mg.

2. A method for the treatment of arterial hypertension as defined in claim 1 wherein the amount of chlorthalidone administered is from 3.0 to 7.5 mg daily.

3. A method for the treatment of arterial hypertension as defined in claim 1 wherein the amount is 3-3.25 mg daily.

4. A method for the treatment of arterial hypertension as defined in claim 1 wherein the amount is 6-6.25 mg daily.

5. A method for the treatment of arterial hypertension in a patient greater than sixty-five years old, said method comprising orally administering to said patient an initial dose of chlorthalidone of from 2.5-6.25 mg daily.

6. A method for the treatment of arterial hypertension as in claim 5 wherein the chlorthalidone dose is 3-3.25 mg.

7. A method as defined in claim 1 or claim 5 where the chlorthalidone is administered in combination with an additional anti-hypertensive agent.

8. A method as in claim 7 in which chlorthalidone is not combined in the same dosage form with another anti-hypertensive drug.

9. A method as in claim 7 in which chlorthalidone is combined in the same dosage form with another anti-hypertensive drug.

10. A method as in claim 7 in which chlorthalidone is combined with a drug from one or more of the following classes: angiotensin converting enzyme inhibitor, angiotensin receptor blocker, calcium antagonist (calcium channel blocker), aldosterone antagonist, beta blocker, alpha blocker.

11. A method as in claim 10 in with chlorthalidone is combined with one or more of the following drugs or a pharmaceutically acceptable salt thereof:
   A) Angiotensin converting enzyme inhibitor: Lisinopril, enalapril, ramipril, perindopril, benazepril, captopril;
   B) Angiotensin receptor blocker: Losartan, candesartan, valsartan, irbesartan, telmisartan, eprosartan;
   C) Calcium antagonist: Amlodipine (racemic), S-amlodipine, lacidipine, lercanidipine, manidipine, azelnidipine;
   D) Aldosterone antagonist: Spironolactone, canrenone, eplerenone;
   E) Beta blocker: Carvedilol, nebivolol, atenolol, metoprolol, betaxolol, bisoprolol;
   F) Alpha blocker: Terazosin, doxazosin, prazosin.

* * * * *

UNITED STATES PATENT AND TRADEMARK OFFICE
CERTIFICATE OF CORRECTION

PATENT NO. : 7,625,940 B2 Page 1 of 1
APPLICATION NO. : 11/173544
DATED : December 1, 2009
INVENTOR(S) : Lawrence Solomon It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1187 days.

Signed and Sealed this

Second Day of November, 2010

David J. Kappos
*Director of the United States Patent and Trademark Office*